Figure 1:
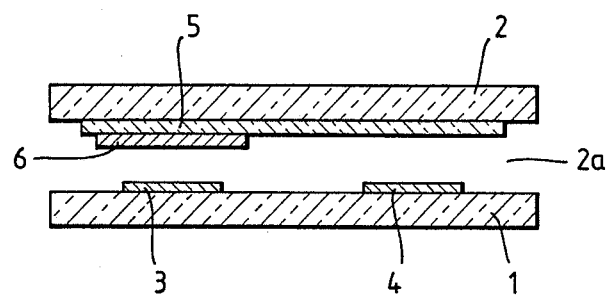

United States Patent [19]

Birth et al.

[11] Patent Number: 4,900,424

[45] Date of Patent: Feb. 13, 1990

[54] ELECTROCHEMICAL MEASUREMENT CELL

[75] Inventors: Brian J. Birth, Chelveston; Ian W. Burns, Huntingdon, both of England

[73] Assignee: Unilever Patent Holdings B.V., Rotterdam, Netherlands

[21] Appl. No.: 225,751

[22] PCT Filed: Nov. 30, 1987

[86] PCT No.: PCT/GB87/00857

§ 371 Date: Sep. 28, 1988

§ 102(e) Date: Sep. 28, 1988

[87] PCT Pub. No.: WO88/04048

PCT Pub. Date: Jun. 2, 1988

[30] Foreign Application Priority Data

Nov. 28, 1986 [GB] United Kingdom ............... 8628531
Nov. 2, 1987 [GB] United Kingdom ............... 8725601

[51] Int. Cl.$^4$ ............................................ G01N 27/30
[52] U.S. Cl. .................................... 204/409; 204/1 T; 204/433; 204/435
[58] Field of Search ............... 204/409, 433, 435, 1 H

[56] References Cited

U.S. PATENT DOCUMENTS 4,454,007 6/1984 Pace .................................... 204/1 T

FOREIGN PATENT DOCUMENTS 0170375 2/1986 European Pat. Off. .
0186286 7/1986 European Pat. Off. .
742588 1/1933 France .
2554593 5/1985 France .

OTHER PUBLICATIONS

Arao Itano, Comptes Rendus des Trauaux do Laboratoire de Carlsborg, vol. 22, pp. 235-237, (1938).
J. Livingston et al., The Electrochemical Soc., Preprint 61-17, pp. 199-218, (1932).
E. Newbery, The Electrochemical Soc., Preprint 65-9, pp. 107-113, (1934).

Primary Examiner—G. L. Kaplan
Attorney, Agent, or Firm—Cushman, Darby & Cushman

[57] ABSTRACT

An electrochemical cell comprising two electrodes, wherein one of said electrodes is suitable for use as a reference electrode in electrochemical measurements, said device comprising (a) a capillary fill cell capable of receiving a small volume of aqueous sample liquid, said cell incorporating (b) a redox electrode located within said capillary fill cell, and (c) a reagent layer comprising quinhydrone located in said cell in a dry adherent water-soluble layer adherent to an inner surface of said cell opposite to or overlying said redox electrode and capable of dissolving during use in aqueous sample liquid in the region of said redox electrode.

11 Claims, 2 Drawing Sheets

ELECTROCHEMICAL MEASUREMENT CELL

This invention relates to electrochemical measurement devices and methods, especially for pH measurement.

Measurement of pH is known to be possible in a variety of ways. A widely-used technique is based on the glass pH electrode, used in conjunction with a reference electrode. Glass pH electrodes are fragile and call for the use of high-impedance electronic instrumentation circuitry engineered to exacting standards.

An early electrochemical method of pH measurement was based on the reversible redox system p-benzoquinone (quinone) and its hydroquinone (quinol), involving production and consumption of protons.

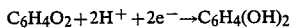

$$C_6H_4O_2 + 2H^+ + 2e^- \rightarrow C_6H_4(OH)_2$$

An inert electrode, dipping into the solution under test with the addition of excess of the sparingly soluble quinone/quinol mixture, will assume a potential governed by the activity of $H^+$. This potential can be measured by the inclusion of a conventional reference electrode (e.g. saturated KCl calomel) into the solution, both electrodes connected to a suitable voltmeter. The potential difference at the voltmeter is related to the $H^+$ activity via the Nernst equation in the following forms:

$$\Delta E = \Delta E° + \frac{RT}{F} \ln a_{H+}$$

or $$\Delta E = \Delta E° - \frac{RT}{F} \cdot (pH)$$

The quinhydrone electrode as described above has fallen from favour since about 1928 due to the emergence of practical glass electrodes, owing to the fact that the glass electrode was non-destructive of the liquids to be tested, while the quinhydrone technique required quantities of the liquids under test to be mixed with quinhydrone.

It is an aim of the present invention to provide new robust and convenient arrangements applicable to pH measurement, and to the production of reference electrodes, usable for other electrochemical measurements.

In particular, it is an aim of the present invention to provide arrangements for pH measurement which can be implemented with simplified electronic instrumentation.

It is a further aim of the invention to provide pH measurement cells which give useful consistency and accuracy in measurement in spite of manufacturing variations.

A particular aim of the invention is to provide electrochemical measurement cells which can be made cheaply enough to be single-use disposable devices, in contrast to usual expensive measurement electrodes. Another aim is to provide electrodes and measurement cells that can be manufactured with only small batch-to-batch and within-batch variations. A related aim is to provide electrodes and measurement cells that can be used without individual standardisation and compensation for voltage offset.

According to an aspect of the invention there is provided an electrochemical cell comprising two electrodes, wherein one of said electrodes is suitable for use as a reference electrode in electrochemical measurements, said device comprising (a) a capillary fill cell capable of receiving a small volume of aqueous sample liquid, said cell incorporating (b) a redox electrode located within said capillary fill cell, and (c) a reagent layer comprising quinhydrone located in said cell in a dry adherent water-soluble layer adherent to an inner surface of said cell opposite to or overlying said redox electrode and capable of dissolving during use in aqueous sample liquid in the region of said redox electrode.

Such an electrochemical device can further comprise (d) a reagent layer comprising pH buffer material located in said cell in a dry adherent water-soluble layer adherent to an inner surface of said cell opposite to or overlying said redox electrode and capable of dissolving in aqueous liquid in the region of said redox electrode, thereby to render said redox electrode useful as a reference electrode.

One of said electrodes can be a reference electrode, and a further electrode can in that case constitute said redox electrode (c) and has associated therewith said reagent layer (d) comprising quinhydrone, thereby to render said cell suitable for the measurement of pH in a small quantity of aqueous liquid sample. For example, in one related embodiment a cell suitable for the measurement of pH in a small quantity of aqueous liquid sample comprises (a) a capillary-fill cell, said cell incorporating (b) two redox electrodes of similar construction to each other formed as laterally-spaced layers of electrode material each adherent to a wall of said cell, said cell also incorporating (c) a reagent layer comprising quinhydrone located in said cell in a dry adherent water-soluble layer adherent to an inner surface of said cell opposite to or overlying each of said redox electrodes and capable of dissolving in aqueous liquid in the region of said redox electrodes, and (d) a reagent layer comprising pH buffer material in dry form located in said cell in the region of one only of said two electrodes.

In a further embodiment, said reference electrode is a halide-sensitive metal-metal-halide electrode, such as a chloride-sensitive reference electrode with which is associated a reagent layer comprising a standard quantity of soluble halide ion such as chloride ion in the form of a dry adherent water-soluble layer adherent to an inner surface of said cell opposite to or overlying said metal-metal-halide electrode and capable of dissolving in aqueous liquid in the region of said metal-metal-halide electrode.

In devices according to the invention, said capillary fill cell can have a width of up to about 150 microns, e.g. up to about 100 microns. The width is not particularly critical, but wider cells of larger volume involve the use of longer reaction times and may make it desirable to use relatively large lateral spacings between the electrodes.

At least one of said electrodes can comprise a screen-printed layer of conductive particles, such as particles of silver, gold, platinum, or graphite, adherent to a wall of said capillary fill cell. Said conductive particles can optionally be further overlaid with carbon particles.

A device according to the invention can have reagent layer(s) comprising a screen-printed layer of reagent material together with a thickener (e.g. nitrocellulose or polyvinylpyrrolidone) either adherent to a wall of said capillary fill cell opposite to one said electrode or overlying one said electrode. The respective reagents including quinhydrone and pH buffer material or for example water-soluble halide can in suitable cases be present in either separately formed reagent layers or in a mixed reagent layer.

A capillary fill cell here means a chamber defined between closely spaced opposite plates fixed together to receive a small liquid sample of defined volume. In this invention, either or each of said plates carries one or more films or layers of electrode material and/or soluble reagents: relevant reagents are materials which in use are to react with said electrodes or otherwise affect the electrode processes. Generally the electrodes are laterally spaced from one another to leave for each electrode a separate overlying portion of the volume of said capillary fill cell wherein an electrode reaction proper to the respective electrode can take place, and the preferred form of electrode is as a screen-printed layer of electrode material adherent to an inner surface of a wall of said cell and located in laterally spaced relation from the other electrode(s) of said cell.

According to one form of the present invention we also provide an electrochemical device suitable for measurement of pH in a small quantity of aqueous liquid sample, said device comprising a capillary-fill cell incorporating two identical redox electrodes, sufficient quantity of quinhydrone in dry form capable of dissolving in aqueous liquid in the region of the electrodes plus a quantity of pH buffer salt in the region of one electrode only.

Further, we provide an electrochemical half-cell which can be used as a reference element in a variety of electrochemical measurements, said cell comprising one half of a CFD containing an inert redox electrode, quinhydrone and buffer layer. Connection to the other half of the CFD (which can contain any of a variety of measurement structures (e.g. electrode(s) and any non-identical releasable reagents) can be made (as in the pH device) by virtue of a quasi-stable liquid-liquid interface, formed at the junction of the half-cells by the two dissimilar liquid fillings. The potential (liquid-junction potential) arising at this interface is well-defined and can—in this cell configuration—be well calculated, in distinction from the junction potentials of many other forms of cell.

References to quinhydrone herein refer to a composition comprising sufficient quinol and quinone to establish a defined redox potential at the electrode, and are not limited to a 1:1 mixture of quinol and quinone. It is to be noted throughout that the quantities of quinol and quinone needed for performance of the invention described herein are not limited to saturated and near-saturated solutions: any concentrations sufficient to define a cell potential can be used. In place of benzoquinone and its corresponding quinol, other quinones such as 1,4 naphthoquinone, tetrachlorobenzoquinone, thymoquinone, toluquinone can be used, and their alternative use is to be understood throughout.

Cells according to the invention can include any of a number of additional electrodes, releasable layers, or immobilised layers, depending on the particular specificity in view.

The reference or pH electrode can for example be constituted by a film deposited on an inner surface of the capillary fill cell, e.g. a film of graphite particles or noble-metal particles in a plastics or resin matrix.

Miniature measurement cells made according to this plan can be provided in single-use disposable form.

The cells can be provided with convenient connectors to allow them to interengage with contacts of an electronic measuring instrument.

The instrument can comprise a relatively low-impedance millivoltmeter or amperometer circuit. Since the electrodes etc. are identically similar, due to the fabrication technique employed, no calibration is required.

Figure 2:
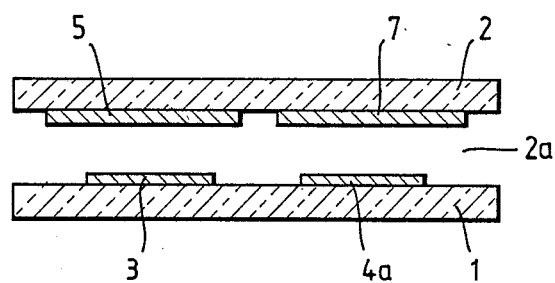
Figure 3:
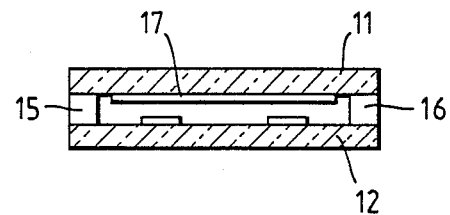
Figure 4:
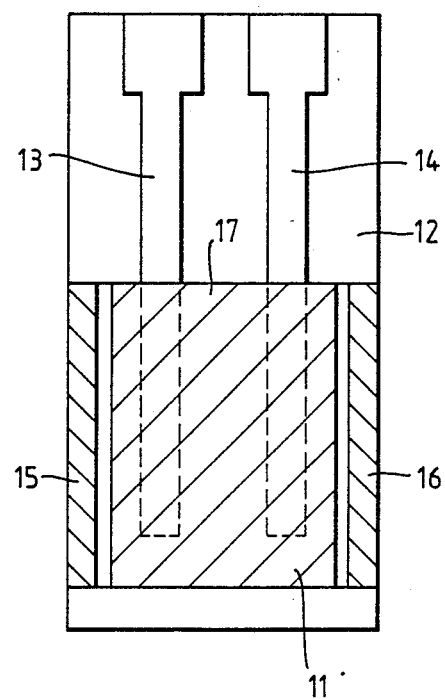

Embodiments of the invention are further illustrated with reference to the following examples and accompanying drawings, in which FIG. 1 shows in diagrammatic and fragmentary cross-section an electrochemical pH measurement device, as in Example 1 below;

FIG. 2 shows in diagrammatic and fragmentary cross-section a cell including a half-cell reference element according to an embodiment of the invention as in Example 2 below; and FIGS. 3 and 4 show, respectively in section and diagrammatic plan, an example of a presently preferred electrochemical device according to an embodiment of the present invention.

EXAMPLE 1

This example illustrates the preparation and use of an electrochemical pH measurement device comprising a quinhydrone electrode confined within a capillary fill cell device. In the device of this example, the capillary cell contains electrodes of two similar materials, graphite. A concentration of quinhydrone in the region of both of the electrodes is provided in use by means of a dry preparation located in a limited region near the electrodes.

Electrodes are prepared for this example by screen-printing an ink comprising a suspension of graphite particles in a curable liquid resin vehicle (ink product No. R-4800 available from Johnson Matthey Chemicals Ltd) as used for the production of polymer thick film resistors, on to a pvc sheet substrate, through a 230 mesh 23 micron emulsion screen. The printed material is allowed to cure at least 24 hours at room temperature before further use.

In this example the graphite layers are formed as 1.55 mm by 33 mm stripes on the pvc substrate, each terminated by a 7 mm $\times$ 10 mm pad for making external electrical contacts. The stripes are arranged as a parallel pair spaced apart by about 8 mm.

In this example a pair of graphite electrodes is intended to be used as a pH measurement cell. Accordingly, one of the electrodes of the pair is set up as a reference electrode. This can be conveniently achieved by associating one of the electrodes with a limited region of dry material to yield a pH buffer when taken up into the liquid to be tested. The location of the dry material and the size chosen for the cell are such that inappreciable diffusion of the buffer material to the measurement electrode takes place during the time of the measurement.

A suitable buffer material is made and located by screen-printing a solution containing e.g. 50 ml of 2.5M tris(hydroxymethylaminomethane), adjusted to pH 8 with hydrochloric acid, for each 50 g of polyvinylpyrrolidone (pvp) (m.w. 44,000), on to the desired location of a transparent pvc plate which is to be used as a wall of the cell opposite to the wall that carries the electrodes, and drying the print at room temperature in air. Equimolar sodium dihydrogen and disodium hydrogen phosphate buffer can be used instead of tris.

An overall dried layer of quinhydrone is applied by screen-printing a mixture comprising quinhydrone, saturated aqueous solution, 1 part by volume, and pvp, 1 part by weight, over the pvc substrate sheet carrying the particulate graphite electrodes, or over the opposite face of the cell, either before or after the limited region of dry material to yield pH buffer is applied to correspond with the position of one only of the electrodes.

A capillary-fill cell is then assembled by securing the top plate over the printed electrodes at 90 micron spacing, in such an orientation that the dry buffer material printed on the plate opposite the electrodes overlies only one of the electrodes and is spaced laterally away from the other electrode.

The physical arrangement of the cell described in this example can be as shown in FIG. 1 of the accompanying drawings. In FIG. 1 there is shown a capillary-fill cell in section. The general construction of the cell can show many of the features described and illustrated in EP No. 0 170 375, but for present purposes it is enough to indicate a first glass or plastics or ceramic wall 1 and a second wall 2 which are closely spaced apart substantially parallel to leave a thin volume 2a between them, which in use can be filled with for example aqueous sample liquid. The details by which wall 1 and wall 2 can be fixed together with spacer side walls to define a cell chamber of for example standardised thickness of the order of 100 microns is described e.g. in EP No. 0 170 375.

The electrodes described above are indicated as electrode layers 3 and 4 in FIG. 1. Ohmic connections to external circuitry, especially a voltage measurement device, can be per se conventional and are not shown. A layer shown at 5 on wall 2 is a dried layer of quinhydrone as described above, and a layer shown as 6 is a dried layer of the buffer material as described above, in this case overlying layer 5 and opposing electrode 1 only.

The construction is found to constitute a convenient and disposable pH measurement cell.

EXAMPLE 2

This example illustrates the preparation and use of the quinhydrone electrode as a half-cell reference element in a CFD with a dissimilar electrode for the measurement of chloride ion.

The general construction can be as shown in FIG. 2, which corresponds to FIG. 1 except that the quinhydrone layer 5 incorporates a buffer material and opposes only reference electrode 3, and an electrode 4a is provided which may be of a similar or different type than electrode 3, often a dissimilar type, according to the purpose of the cell, and an optional reagent layer 7 opposing electrode 4a, to provide any reagent material needed in association therewith.

For example, if electrode 4a is a chloridised silver electrode, (e.g. of a form of construction as described in EP No. 0 186 286) then layer 7 can be a dried chloride-containing material.

Useful embodiments of the invention have provided cells with carbon-particle electrodes made in the manner described herein, and having for example electrode resistances of the order of e.g. 5 ohms or less, by suitable upward adjustment of the graphite content of the material applied to form the electrodes. Conductivities per unit area of for example 100–200 mmhos/cm$^2$ have been achieved and found useful, though for certain purposes electrode resistances of the order of 1000 ohms can be acceptable.

In certain embodiments of the invention, carbon-particle-containing electrode layers can usefully overlie silver- or silver-particle-based electrodes to give very low resistances e.g. 1 to 2 ohms, especially useful for amperometric cells.

Of course, the invention extends to the use of a wide variety of auxiliary material arrangements, including the use of platinum, gold, silver or copper, e.g. in continuous form or in particle form embedded in a matrix, e.g. based on pvc with plasticiser as matrix material. Metal particles and carbon particles, where present together, can be either inter-mixed in their matrix, or present in adjacent overlying layers with or without intermixture at the interface, and the metal particles, e.g. silver, may include chloridised or chloride particles.

Among the further arrangements contemplated are 3-electrode arrangements for amperometry including a reference electrode as described herein, with a working electrode and counter-electrode either of similar or different material.

Also optionally present in association with the electrodes, and cells containing them can be auxiliary structure for supplying or withdrawing reagents and sample materials, e.g. filters, gels, and/or porous and/or membranous and/or selectively-permeable plugs, reservoirs and partitions.

FIGS. 3 and 4, show respectively in section and diagrammatic plan, an example of a presently preferred electrochemical device according to an embodiment of the present invention, which can be made in a form which is robust, convenient and with reproducible properties, in this example suitable for the measurement of pH and including a quinhydrone reference electrode.

The top and bottom plates 11 and 12 are each made of sheet pvc material.

A carbon electrode 13 is formed on the bottom plate by a layer of screen-printing ink containing carbon particles (Johnson Matthey R4800 carbon ink). A silver electrode 14 is also formed on the bottom plate by a layer of screen- printing ink containing silver particles (Johnson Matthey silver ink P1856). Electrodes 13 and 14 are laterally spaced apart by at least about 0.5 cm. Silver chloride is formed on said silver electrode by exposure to aqueous 0.1M HCl with 1M hydrogen peroxide for 4 minutes.

The top and bottom plates 11 and 12 are secured together in closely spaced parallel relation by two portions 15, 16 of a double-sided adhesive tape of thickness about 90 microns. Top plate 11 is of lesser size than bottom plate 12, to leave on bottom plate 12 an overhang at one end to provide for handling and connectors for the electrodes, and a small overhang at the other end to provide for sample uptake by capillary action. The active cell which in use is filled by contact with sample liquid to take up a volume defined by the capillary effect is substantially the volume between plates 11 and 12 as shown.

Alternative materials for adhesion and spacing of plates 11 and 12 can be as mentioned for example in EP Nos. 0 171 148 or 0 170 375.

The illustrated example of a cell corresponds to a sample size of about 45 microliter. The dimensions can easily be chosen to accommodate a substantial range of small-scale sample volumes as desired.

The top plate has a layer 17, comprising salt and quinhydrone, formed thereon. Layer 17 is opposite to the respective portions of electrodes 13 and 14 within the cell formed by plates 11 and 12 so that sample liquid within the cell can dissolve material from the layer into the respective portions of sample liquid overlying the electrodes. Layer 17 is formed by screen-printing a non-aqueous composition comprising finely divided particles (ball-milled to a particle size less than about 10 micron) of quinhydrone (2% w/w) and sodium chloride (58.8% w/w) in a solution (39.2% w/w) of cellulose acetate (10% w/v) in cyclohexanone, made and applied in the manner described in copending European application No. 8730969.1 dated Nov. 2, 1987 (and Intl. No. PCT/GB/87/0770, and GB No. 87 25601, the priority of which is also claimed herein), to leave a dry film at a density of about 3 mg per sq cm comprising sodium chloride 91%, quinhydrone 3% and cellulose acetate 6%.

The layer of salt and quinhydrone can afterwards be sprayed lightly with a surfactant such as for example 2% w/w Triton-X-100 surfactant in propan-1-ol.

(As the pH goes up, the cell potential goes down: in one example of such a cell the following measurements were obtained:

| pH | | millivolts | |
|---|---|---|---|
| | 6.52 | | 143 |
| | 5.11 | | 200 |
| | 4.03 | | 254 |
| | 3.04 | | 308 |
| | 2.15 | | 360.) |

The quinhydrone electrode in practice is best used at pH values not more than about pH 8.

When a number of electrodes according to this embodiment were made as a batch, it was found on one occasion that the variation of cell potential between examples was at most 0.1 mV.

The several features described herein, including those illustrated in and by the drawings and Examples, are disclosed and can be used in any desired combination or subcombination.

We claim:

1. An electrochemical device comprising two electrodes, wherein one of said electrodes is suitable for use as a reference electrode in electrochemical measurements, said device comprising (a), a capillary fill cell capable of receiving a small volume of aqueous sample liquid, said cell incorporating (b) a redox electrode which may be the reference electrode located within said capillary fill cell, and (c) a reagent layer comprising quinhydrone located in said cell in a dry adherent water-soluble layer adherent to an inner surface of said cell opposite to or overlying said redox electrode and capable of dissolving during use in aqueous sample liquid in the region of said redox electrode.

2. An electrochemical device according to claim 1, further comprising (d) a reagent layer comprising pH buffer material located in said cell in a dry adherent water-soluble layer adherent to an inner surface of said cell opposite to or overlying said redox electrode and capable of dissolving in aqueous liquid in the region of said redox electrode, thereby to render said redox electrode useful as a reference electrode 3. An electrochemical device according to claim 1, wherein one of said electrodes is a reference electrode and a further electrode constitutes said redox electrode (c) and has associated therewith said reagent layer (d) comprising quinhydrone, thereby to render said cell suitable for the measurement of pH in a small quantity of aqueous liquid sample.

4. An electrochemical device according to claim 3, comprising a cell suitable for the measurement of pH in a small quantity of aqueous liquid sample, said device comprising (a) a capillary-fill cell, said cell incorporating (b) two redox electrodes of similar construction to each other formed as laterally-spaced layers of electrode material each adherent to a wall of said cell, said cell also incorporating (c) a reagent layer comprising quinhydrone located in said cell in a dry adherent water-soluble layer adherent to an inner surface of said cell opposite to or overlying each of said redox electrodes and capable of dissolving in aqueous liquid in the region of said redox electrodes, and (d) a reagent layer comprising pH buffer material in dry form located in said cell in the region of one only of said two electrodes.

5. An electrochemical device according to claim 3, wherein said reference electrode is a halide-sensitive metal-metal-halide electrode, with which is associated a reagent layer comprising a standard quantity of soluble halide ion in the form of a dry adherent water-soluble layer adherent to an inner surface of said cell opposite to or overlying said metal-metal-halide electrode and capable of dissolving in aqueous liquid in the region of said metal-metal-halide electrode.

6. An electrochemical device according to claim 1, wherein said capillary fill cell has a width of up to about 150 microns.

7. An electrochemical device according to claim 1, wherein at least one of said electrodes comprises a screen-printed layer of conductive particles adherent to a wall of said capillary fill cell.

8. An electrochemical device according to claim 7, wherein said conductive particles comprise particles selected from graphite, silver, gold or platinum, optionally overlaid with carbon particles.

9. An electrochemical device according to claim 1 wherein said reagent layer comprises a screen-printed layer of reagent material together with a thickener either adherent to a wall of said capillary fill cell opposite to one said electrode or overlying one said electrode.

10. An electrochemical device according to claim 9, wherein said thickener comprises polyvinylpyrrolidone.

11. An electrochemical device according to claim 9, wherein a reagent layer comprising quinhydrone also comprises a pH buffer material or a water-soluble halide.

* * * * *